US006377057B1

(12) United States Patent
Borkholder (10) Patent No.: US 6,377,057 B1
(45) Date of Patent: Apr. 23, 2002

(54) CLASSIFICATION OF BIOLOGICAL AGENTS ACCORDING TO THE SPECTRAL DENSITY SIGNATURE OF EVOKED CHANGES IN CELLULAR ELECTRIC POTENTIAL

(75) Inventor: David Borkholder, San Jose, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 09/251,027

(22) Filed: Feb. 18, 1999

(51) Int. Cl.[7] ................................................ F02P 17/00
(52) U.S. Cl. ........................ 324/692; 324/447; 800/2; 435/7.1; 435/173.1; 435/173.4; 435/285.2; 435/287.1; 435/325; 514/44
(58) Field of Search ................ 435/287.1, 7.1, 435/173.1, 173.4, 285.2, 325; 800/2; 514/44; 324/447, 692

(56) References Cited

U.S. PATENT DOCUMENTS 5,981,268 A * 11/1999 Kovacs et al.

OTHER PUBLICATIONS

Pancrazio et al., *Annals of Biomedical Engineering*, 27(6):697–711, 1999.*
Stern et al., *J. of Neurophysiology*, 77(4):1697–1715, 1997.*
Connolly, P., et al., "An Extracellular Microelectrode Array For Monitoring Electrogenic Cells In Culture," *Biosensors & Bioelectronics* (1990) vol. 5:223–234.
Gross, Guenter W., et al., "The Use of Neuronal Networks On Multielectrode Arrays As Biosensors," *Biosensors & Bioelectronics* (1995) vol. 10:553–567.
Hickman, J.J., et al., "Whole Cell Based Biosensors," 207th *ACS National Meeting, American Chemical Society*, San Diego, California, Mar. 13–17, 1994.
Israel, D.A., et al., "Time Delays In Propagation Of Cardiac Action Potential," *American Journal Of Physiology: Heart and Circulatory Physiology* , (Jun. 1990) vol. 27, No. (6):H1906–H1917.
Oberg, Ake, et al., "Fourier Analysis Of Cardiac Action Potentials," *J. Electrocardiology* (1981) vol. 14, No. (2) :139–142.
Rasmusson, R.L., et al., "A Mathematical Model Of Electrophysiological Activity In A Bullfrog Atrial Cell," *American Journal Of Physiology* (1990) vol. 259:H370–H389.
Borkholder, David A., et al., "An Approach To The Classification of Unknown Biological Agents with Cell Based Sensors," *Solid–State Sensor and Actuator Workshop*, Hilton Head Isalnd, South Carolina, Jun. 8–11, 1998.

* cited by examiner

Primary Examiner—Marianne P. Allen
(74) Attorney, Agent, or Firm—Pamela J. Sherwood; Bozicevic, Field & Francis LLP (57) ABSTRACT

Biologically active compounds are classified according to their effect on ion channels, changes in membrane potential and ionic currents, and the frequency content of action potentials that the compound(s) evoke in excitable cells. The spectral density changes of such evoked membrane potential or action potential are a characteristic for each channel type that is modulated by the test compound. A pattern of spectral changes in membrane potential is determined by contacting a responsive cell with a compound, and monitoring the membrane potential or ionic currents over time. These changes correlate with the effect of that compound, or class of compounds, on the ion channels of the responding cell. This pattern of spectral changes provides a unique signature for the compound, and provides a useful method for characterization of channel modulating agents.

16 Claims, 6 Drawing Sheets

CLASSIFICATION OF BIOLOGICAL AGENTS ACCORDING TO THE SPECTRAL DENSITY SIGNATURE OF EVOKED CHANGES IN CELLULAR ELECTRIC POTENTIAL

This invention was made with support from the DARPA MicroFlumes Program, Contract number N66001-96-C-8631. The Government may have certain rights in this invention.

BACKGROUND OF THE INVENTION

Cell based sensor technologies utilizing electrically active living cells cultured on extracellular electrode arrays have been a focus of research since 1972 (Thomas et al. (1972) *Experimental Cell Research* 74:61–66). However, most efforts have been directed towards pure neuroscience applications that require experienced interpretation of the signals. More recent work by some groups has attempted to expand the practical uses of action potential (AP) based systems to environmental and chemical monitoring and pharmaceutical screening. However, there has been little work done on signal interpretation models for general classification of agents modulating cellular electrical characteristics.

The membrane capacitance, membrane conductance, cell/substrate separation and action potential parameters of a cell are significant markers regarding a cell's metabolic state, including general cellular health and ionic channel activity. The membrane potential, the voltage difference across a cell's plasma membrane, depends on the distribution of ionic charge. For example, in a metallic conductor, the mobile particles carrying charge are electrons; in an aqueous solution, the mobile particles are ions such as $Na^+$, $K^+$, $Cl^-$, and $Ca^{++}$. In an aqueous solution, the number of positive and negative charges are normally balanced exactly, so that the net charge per unit volume is zero. An unbalanced excess of positive charges creates a region of high electrical potential, repelling other positive charges and attracting negative charges. An excess of negative charges repels other negative charges and attracts positive charge. When an accumulation of positive charges on one side of a membrane is balanced by an equal and opposite accumulation of negative charges on the other side of the membrane, a difference of electrical potential (voltage) is set up between the two sides of the membrane.

Charge is carried back and forth across the cell membrane by small inorganic ions. These can traverse the lipid bilayer only by passing through special ion channels or pumps. When the ion channels open, the charge distribution shifts and the membrane potential changes. Of these ion channels, those whose permeability is regulated are the most significant; these are referred to as gated channels. Two classes of gated channels are of crucial importance: (1) voltage-gated channels, where the transmembrane potential controls the permeability of the channel; and (2) ligand gated channels, where the channel is opened (or closed) by binding of a chemical messenger to a receptor site.

Electrical activity in cells is generated by a complex interaction of both ligand and voltage gated ion channels. As a cell depolarizes (transmembrane potential changes), the voltage threshold for opening of different ion channels is reached, resulting in electrochemical gradient driven flow of ions through the cell membrane. Different channel classes open at different times and contribute to unique portions of this action potential. For example, a cardiac action potential can be divided into several phases: an initial rapid depolarization due to increased $Na^+$ conductance; a plateau phase due to the slow opening of voltage-gated $Ca^{++}$ channels; and the final repolarization due to the closure of $Ca^{++}$ channels and the prolonged opening of $K^+$ channels. Most, if not all, ion channels are modulated by signal transduction mechanisms that shape the action potential. For example, in the heart, six principal ion currents contribute to the nodal and pacemaking cell action potential and ten underlie the myocardial action potential.

Ion channels are multi-subunit, membrane bound proteins. In humans, ion channels comprise extended protein families with hundreds, or perhaps thousands, of both closely related and highly divergent family members. These channel superfamilies can be broadly classified into groups, based upon the specific ion, the type of gating, and the number of transmembrane domain segments and pore segments in the mature protein. The functional protein is a multimer that comprises one or more types of alpha subunits, and which are frequently associated with auxiliary, β subunits.

The effect of a compound on ion channels, and on the action potential of a living cell, can provide useful information about the classification and identity of the compound. Methods and means for extracting such information are of particular interest for the analysis of biologically active compounds, with specific applications in pharmaceutical screening, drug discovery, environmental monitoring, biowarfare detection and classification, and the like.

Relevant Literature

Examples of whole cell based biosensors are described in Gross et al. (1995) *Biosensors and Bioelectronics* 10:553–567; Hickman et al. (1994) *Abstracts of Papers American Chemical Society* 207(1–2):BTEC 76; and Israel et al. (1990) *American Journal of Physiology:Heart and Circulatory Physiology* 27(6):H1906–H1917.

Connolly et al. (1990) *Biosens Bioelectron* 5(3):223–34 describe a planar array of microelectrodes developed for monitoring the electrical activity of cells in culture. The device allows the incorporation of surface topographical features in an insulating layer above the electrodes. Semiconductor technology is employed for the fabrication of the gold electrodes and for the deposition and patterning of an insulating layer of silicon nitride. The electrodes were tested using a cardiac cell culture of chick embryo myocytes, and the physical beating of the cultured cells correlated with the simultaneous extracellular voltage measurements obtained.

The molecular control of cardiac ion channels is reviewed by Clapham (1997) *Heart Vessels Suppl* 12:168–9. Oberg and Samuelsson (1981) *J Electrocardiol* 14:13942, perform fourier analysis on the repolarization phases of cardiac action potentials. Rasmussen et al. (1990) *American Journal of Physiology* 259:H370–H389, describe a mathematical model of electrophysiological activity in bullfrog atria.

SUMMARY OF THE INVENTION

Methods and apparatus are provided for the classification of biologically active molecules according to their effect on ion channels, changes in membrane potential, and the shape of action potentials that they evoke. A compound to be tested is put in contact with a biosensor, which has both living and non-living components. The living component comprises cells capable of excitation, which have a plurality of functional ion channels, and the non-living component comprises a means of monitoring changes in electric potential or ionic currents across the cell's membrane. The test compound elicits a characteristic change in the shape and pattern of the membrane potential in the cell, over a range of frequencies.

The changes in electric potential or ionic current are recorded, and the data used to determine the spectral changes that are generated. In a preferred embodiment, the data is digitized and converted to a power spectral density (PSD). The spectral changes may be compared to those found with a control compound or condition, e.g. the absence of the compound. Unknown compounds may be identified by matching the characteristic spectral changes or pattern of spectral changes across a band of frequencies, as compared to a known reference pattern. Alternatively, unknown or known compounds, including derivatives and analogs of pharmaceutically active compounds, are classified as to general type, with respect to ion channel activation according to the particular pattern of responses that the compound evokes.

In one embodiment of the invention, the biosensor comprises cells grown on a microfabricated array having microelectrodes disposed over a substrate, with each microelectrode individually connected via conductive traces to contact points for electrical connection of external circuits.

In another embodiment of the invention, the biosensor comprises a panel of cells comprising different combinations of ion channels. A number of different panels are useful, including but not limited to panels having one type of cell from a variety of species, e.g. cardiac cells from multiple sources; different types of excitable cells from one or more species, e.g. neural, cardiac and sensory cells; and genetically engineered cells that either express ion channels not normally present in that cell type, or that lack expression of specific channels.

DETAILED DESCRIPTION OF THE INVENTION

Methods are provided for classifying and identifying biologically active compounds according to their effect on ion channels, changes in membrane potential and ionic currents, and the frequency content of action potentials that the compound(s) evoke in excitable cells. The frequency content may be further correlated with modulation of specific ion channel classes by the compound.

The spectral density of the evoked membrane potential or action potential change in a characteristic way for each channel type that is modulated by the test compound. A pattern of spectral changes in membrane potential is determined by contacting a responsive cell with a compound, and monitoring the membrane potential or ionic currents over time. These changes correlate with the effect of that compound, or class of compounds, on the ion channels of the responding cell. Additional information is provided by varying the compound and/or the responding cell. This pattern of spectral changes provides a unique signature for the compound. Matching the spectral change pattern of a test compound with the spectral change pattern for reference compounds provides a useful method for characterization of channel modulating agents.

The methods of the invention are a valuable tool that can aid in the selection and prioritization of compounds from large compound collections for biological testing. The effect of a compound on the electrical activity of living cells can be classified in terms of the mechanism of action and may not need competitor assays. Also of interest are remote environmental sensing applications using live cell biosensors, where the general mode of biological action needs to be determined.

DEFINITIONS

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the biosensor" includes reference to one or more biosensors and equivalents thereof known to those skilled in the art, and so forth. All technical and scientific terms used herein have the same meaning as commonly understood to one of ordinary skill in the art to which this invention belongs unless clearly indicated otherwise.

Output signal. The addition of a compound to the environment of a cell will affect certain ion channels, such as ligand gated channels that are activated or blocked in response to the compound. The addition of the compound will also cause further effects because of interactions between channels, e.g. gating of a ligand-gated channel may result in a change in membrane potential which may in turn trigger voltage dependent channels. The combined action of a compound on the complement of ion channels possessed by a single cell provides a unique spectrum of electrical changes, that are reflected in the membrane potential, either as resting potential, subthreshold, or action potential. A recording of these changes over time provides an output signal, which is usually determined as changes in voltage (or ionic current) across the cell membrane, over time. The recorded information can then be digitized, compared to a control output signal, and/or used in conjunction with output signals for the same compound on a cell having a different complement of ion channels.

In many cases the output signal is generated by contacting a compound with the external surface, or external environment of a cell. However, there are also methods known in the art whereby pores are formed in the membrane of cells, which allow agents to enter the interior of the cell. Contacting the internal surface of a cell is desirable for testing compounds that generate an electrical effect after contact with the interior of the cell.

Membrane potential: refers to the electrical potential difference across a cell membrane created by ion transport through channels and pumps in the cell membrane. Some of these channels are passive, so that ions may move through the channel diffusively or by electrical gradient forces acting on them. The electrochemical equilibrium condition that exists is a balance of the diffusion and electrical forces. Others are chemically gated, voltage gated, or have active pumps that move ions across the membrane. Changes in membrane potential can be stimulated by various means, e.g. electrical charge, addition of channel modulating compounds, etc.

Action potential: refers to a sudden change in the electrical state of the cell membrane. For example, the membrane potential may change from about −70 mV to +40 mV during a neuronal cell action potential. A specific series of ion channel events are associated with an action potential. For example, id a neuronal cell voltage gated $Na^+$ channels open when the membrane potential rises about 20 mV above the resting potential; this potential is called the "threshold". Change in membrane potential below this level are referred to as sub-threshold events. $Na^+$ ions rush in for about 1 ms, while positive feedback keeps the channels open until the cell interior becomes positively charged. The $Na^+$ channels close when the voltage peaks, and $K^+$ channels open; these vent $K^+$ into the extracellular fluid. They remain open for about 1.5 ms, until the membrane potential overshoots its initial value slightly. Finally, $Na^+/K^+$ pumps restore the concentrations that existed before firing. Cells capable of action potentials (excitable cells) often have spontaneous potentials and currents when grown in cultured conditions.

Output signal recording. In the methods of the subject invention, responsive cells, usually excitable cells, are grown in culture in such a way that the membrane potential or ionic currents of the cells can be measured, particularly under conditions where the potential is changing, e.g. during an action potential. Exemplary for this purpose are biosensors comprising a cellular component and a transducing means. The transducing means is capable of measuring changes in electric potential or current by optical, chemical, electrical or mechanical means. An example of a transducing means is an electrode.

A number of methods are known in the art for recording the currents and electrical potential changes of cell membranes. These systems may utilize an intracellular or extracellular electrode, preferably an extracellular electrode, operably contacting the cell membrane; and a reference electrode outside of the cell. The electrodes are connected to an amplifying means and a recording means. Typically, the output signal is recorded as changes in voltage (or current) over time. This information can then be digitized for further analysis or analyzed via analog means.

Data analysis: The output signal recording is analyzed by analog or digital methods, as known in the art, to generate a value or series of values herein termed "spectral density signature" (SDS). In a preferred embodiment of the invention, the SDS is the power spectral density, as described below. Alternatively, the SDS is calculated by other methods. For example, analog measurement techniques for real time analysis of an action potential may be used, using the total rms power of the AP as an indicator of general shape, rather than peak to peak amplitude. By examining the rms power in different frequency bands, it may be possible to approximate the power spectral density analysis performed numerically herein.

Data analysis may also include the steps of determining voltage (or current) it change as a function of time, removing outliers, i.e. data deviating from a predetermined statistical distribution, and calculating the density of spectral changes from the remaining data. Standard statistical analysis will typically be included to monitor the reliability of the data.

Power Spectral Density: The power spectral density is calculated by methods known in the art. For example, one may first apply a Hanning window to the signal output from a single action potential, and then take the fast fourier transform. Multiplication of the resulting complex waveform by its complex conjugate and dividing by the frequency range of the fast fourier transform provides an estimate of the power spectral density for the action potential waveform. Other methods for determining power spectral density are known in the art, for example see Oberg et al., supra.

The complete range of frequencies for the action potential is divided into bins or the purpose of calculating the PSD. The frequencies corresponding to each PSD bin are calculated based on the sampling rate and the total number of samples taken. Conventional methods for sampling may be used, typically at a minimum frequency of 2 times the highest frequency of interest (Nyquest frequency) in order to fully reconstruct the original waveform from the digitally sampled data without losing information. Sampling may be performed at frequencies significantly higher than the Nyquest frequency in order to avoid sample processing to reconstruct the waveform, etc.

The maximum resolvable frequency will be half the sampling frequency. The fourier transform is therefore plotted from a minimum value (usually zero) to the maximum resolvable frequency. The bin size is then determined by the length of the data stream. Preferably a longer data sample is used in order to have smaller bins, and a higher resolution.

Evaluation of spectral density signature: A single SDS value or curve can be used as a point of comparison for a compound in accordance with the subject methods. It is generally preferred, however, to convert the output signal to an SDS, and then compare that information to a similarly obtained control SDS, generally a negative control, although comparison to positive controls may be used for some purposes. The comparison may be a subtraction of the two values, ratio of the two curves, etc. The negative control SDS will frequently be the SDS for an action potential generated by the responding cells in the absence of the exogenous compound. Generally the negative control will be similar to the test sample with respect to the ionicity of the solution. Various balanced salt solutions that are compatible with the responding cells may be used.

Other values that find use as controls include, without limitation, stimulated action potentials, e.g. by electrical or chemical stimulation; subthreshold changes in membrane potential; and the like. Evaluations may be taken between the SDS obtained with a single compound against two different responding cells, particularly where the cells differ in expression of defined ion channel gene or genes. Where comparisons are going to be made between related or analogous compounds, the control may be the "base" compound, against which analogs are compared.

Modulation reference pattern. The SDS evaluation provides a series of values for the change in spectral density over a number of frequency bins. These values are correlated with the effect of the compound on the membrane potential or current flow of a cell. Each SDS evaluation therefore provides a reference pattern. The reference pattern provides information about the effect of that compound on a cell that has the complement of ion channels that were present in the responding cell. The total information for one or more spectral density signature values for a compound that is used in classification and identification by the subject methods is herein referred to generically as a "modulation reference pattern". When such information is obtained for a test compound, it may be specifically referred to as a "modulation test pattern". The reference pattern or test pattern will comprise at least a one SDS value, and may comprise several SDS values. Frequently, the reference pattern or test pattern will be comprised of one or more PSD values, usually in the form of comparisons made to a control PSD value.

The amount of information in a reference pattern can be expanded by performing additional tests. For any one compound, analyses can be performed by testing the compound against cells having a different complement of receptors; by comparing the compound to different negative controls; by comparing analogous compounds, and the like.

The modulation reference or test pattern will provide for a data array of SDS values, which may be cross-referenced by the different parameters, e.g. the compound that was added to the cells, the range of frequencies for each bin, the responding cell types, the negative controls, etc. Classification and identification of compounds uses this modulation reference pattern for later comparison of test data.

Modulation Reference Pattern Database: A feature of the invention is the generation of a database of SDS reference patterns for a variety of compounds. Such a database will typically comprise SDS reference pattern information as described above, for a number of related compounds. The compounds of interest in a database may be selected and arranged according to various criteria: the types of molecules that are tested, e.g. steroids, antibiotics, neurotransmitters, etc.; by the source of compounds, e.g. environmental toxins, biologically active extracts from a particular animal or cell, etc.; by the action of the compound on ion channels, e.g. $K^+$ channel antagonists, $Ca^{++}$ channel blockers, and the like.

The modulation reference patterns and databases thereof may be provided in a variety of media to facilitate their use. "Media" refers to a manufacture that contains the SDS reference pattern information of the present invention. The databases of the present invention can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure may be chosen, based on the means used to access the stored information. A variety of data processor programs and formats can be used for storage, e.g. word processing text file, database format, etc.

As used herein, "a computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

A variety of structural formats for the input and output means can be used to input and output the information in the computer-based systems of the present invention. One format for an output means ranks PSD patterns possessing varying degrees of similarity to a reference pattern. Such presentation provides a skilled artisan with a ranking of similarities and identifies the degree of similarity contained in the test pattern.

Comparison of reference patterns. The comparison of a modulation test pattern obtained from a test compound and a modulation reference pattern is accomplished by any suitable deduction protocol, AI system, statistical comparison, etc. Methods of searching databases are known in the art. See, for example, U.S. Pat. No. 5,060,143, which discloses a highly efficient string search algorithm and circuit, utilizing candidate data parallel, target data serial comparisons with an early mismatch detection mechanism. For other examples, see U.S. Pat. No. 5,720,009 and U.S. Pat. No. 5,752,019.

As an example, a system may be input by entering the names of the sample files, where the sample files contain the data array for each modulation reference or test pattern. The power values from the sample files are adjusted with a monotonic, variance-stabilizing transformation. Next, the expected signal response for each power value is determined using the data from the sample files. A single regression line is fit to the overall signal strengths of the images and their corresponding adjusted power values. This determines the expected signal response and variance, given the signal strength of the image. Samples of unknowns are assigned to the modulation reference pattern that minimizes the variance of the resulting fits. Reference compounds are assigned to each sample whose compound is unknown along with the probability that the assignment is correct. This probability is computed using the expected signals and variances from the regression fits at the sample's overall signal strength based on a t-distribution.

The spectral data that is obtained from a test compound and reference pattern(s) are compared to determine whether the signals can be superimposed, i.e. whether there is a match between two patterns; or whether they vary. Since a modulation reference pattern and modulation test pattern may be comprised of multiple values, where each comprising a spectral density value for multiple frequencies, the matching may be performed with several different datasets. The evaluation of the data will depend on the type of analysis to be performed.

Where an unknown compound is being tested against a single reference compound, the comparison will typically involve determination of whether there is a statistically significant match for the spectral density at each frequency bin. If multiple comparisons for a single compound are provided, then the determination will be for a statistically significant match for each of the comparisons. When an unknown compound is compared against a database, a more sophisticated search may be required to first determine the reference pattern that is the closest match to the modulation test pattern.

Methods of classifying compounds according to their action may utilize comparison across different parameters than those that are used for identification of unknown compounds. The parameter of interest may not be whether a modulation test pattern matches a reference pattern, but whether the compound shows a difference in, for example, ratios taken against control values when such ratios are obtained with different cell types, different negative controls, etc.

As an example, one may test whether a compound acts as an agonist or antagonist on an ion channel of interest. A database may be set up with PSD ratios that compare the effect of one or more compounds across a range of different cells. These cells may include a native cell type; the same cell type engineered to further comprise an exogenous ion channel of interest; and/or the same cell type engineered to lack an endogenous ion channel of interest. The database of information may then be used to classify cells according to whether or not there is a variation between the response of these different cell types. Such a classification could be used to sort compounds according to their action as agonist, antagonist or neutral with respect to the ion channel of interest. A search of the database with a PSD test pattern from a test compound may be based on whether the test compound shows a similar variation as the reference compounds, and not whether there is an actual match in power values.

Reference Compound: The subject methods are used to analyze a wide variety of compounds in order to establish reference PSD patterns and databases. Molecules of interest for analysis include any biologically active molecule with the capability of modulating directly or indirectly, the activity of an ion channel.

The compounds are typically added in solution, or readily soluble form, to the medium of cells in a biosensor. Usually the compounds are added using a flow through system, or alternatively, adding a bolus of the compound to an otherwise static solution. In a flow-through system, two fluids are used, where one is a salt solution, and the other is the salt solution with the test compound added. The first fluid is passed over the cells, followed by the second. In a single solution method, a bolus of the test compound is added to the volume of medium surrounding the cells. The overall osmolality of the solution should not change significantly with the addition of the bolus, or between the two solutions in a flow through method.

Preferred compound formulations do not include additional components, such as preservatives, that have a significant effect on the overall formulation. Thus preferred formulations consist essentially of a biologically active compound and a physiologically acceptable carrier, e.g. water, ethanol, DMSO, etc. However, if a compound is liquid without an excipient the formulation may consist essentially of the compound itself.

A plurality of assays may be run in parallel with different compound concentrations to obtain a differential response to the various concentrations. As known in the art, determining the effective concentration of a compound typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection.

Compounds of interest encompass numerous chemical classes, though typically they are organic molecules. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Included are pharmacologically active drugs, genetically active molecules, etc. Compounds of interest include chemotherapeutic agents, anti-inflammatory agents, hormones or hormone antagonists, ion channel modifiers, and neuroactive agents. Exemplary of pharmaceutical agents suitable for this invention are those described in The Pharmacological Basis of Therapeutics, Goodman and Gilman, McGraw-Hill, New York, N.Y., (1993) under the sections: Drugs Acting at Synaptic and Neuroeffector Junctional Sites; Drugs Acting on the Central Nervous System; Autacoids: Drug Therapy of Inflammation; Water, Salts and Ions; Drugs Affecting Renal Function and Electrolyte Metabolism; Cardiovascular Drugs; Drugs Affecting Gastrointestinal Function; Drugs Affecting Uterine Motility; Chemotherapy of Parasitic Infections; Chemotherapy of Microbial Diseases; Chemotherapy of Neoplastic Diseases; Drugs Used for Immunosuppression; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," Academic Press, New York, 1992).

Test Compound: Test compounds include all of the classes of molecules described above, and may further comprise samples of unknown content. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest compounds being assessed for potential therapeutic value, i.e. drug candidates.

The term samples also includes the fluids described above to which additional components have been added, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection, usually from about 0.1 $\mu$l to 1 ml of a biological sample is sufficient.

Compounds and candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Excitable cell. The cells that respond to the test and reference compounds will typically be excitable cell, i.e. capable of generating an action potential. Suitable cells include cardiac cells, neuronal cells, sensory cells, etc. The cells may be primary cultures that are set up for short term growth, e.g. cardiac cells from chicks, etc. Such primary cultures can provide highly reproducible results from one culture to another. Alternatively, cell lines are used. Cell lines are generally able to be passaged in culture for extended periods of time. They include, without limit, immortalized cells, stem cells, etc., where the stem cells are able to differentiate into excitable cells suitable for the subject methods. Examples of cultured excitable cells include, but are not limited to, suprachiasmatic neurons (Walsh et al. (1995) *Neuroscience* 69(3):915–29); motoneuronal cultures (Zoran et al. (1996) *Dev Biol* 179(1):212–22); cardiac tissue (Fast and Kleber (1995) *Cardiovasc Res* 29(5):697–707); cardiac ventricular myocytes; Schackow et al. (1995) *Am J Physiol* 268(4 Pt 1):C1002–17; electrogenic myocardiac cells (Connolly et al. (1990) *Biosens Bioelectron* 5(3):223–34).

Panel of excitable cells. The biosensor(s) as used in the methods of the invention may comprise a panel of one or more distinct cell types, where each cell type will be present in either an individual culture plate, separate wells of a single culture plate, or flowing cells through the system. The use of cell panels provides several advantages. It allows for a finer discrimination between compounds, because each different cell type will have a unique complement of ion channels. By selection of cell types based on expression of specific channels, or by genetic manipulation to create cell types that differ in expression of specific panels, the action of a compound on specific ion channels (or the interaction between two ion channels) may be determined. Cells may also be present in one large plate, where a bolus of the agent was injected over discrete regions, where diffusion of the compound to an adjacent "virtual" well is much slower than the response time.

Panels of cell may comprise single types of cells, e.g. cardiac, neural, glial, muscle, sensory, etc. obtained from different sources, i.e. different tissues, species, etc. Alternatively, panels may comprise a single cell type that is genetically altered as to expression of particular ion channels, beta subunits associated with channels, or receptors associated with channels. Other panels of interest comprise multiple cell types from a single source, e.g. frog muscle, cardiac and neural cells; or merely an assortment of different cell types.

Genetically modified cells: For various purposes it is desirable to utilize cells comprising an altered complement of ion channels, either through deletion or addition of expressed channel genes. Such genetic manipulation may be performed in vitro, on cultured cells, particularly where the cells are maintained as a long term cell line. Alternatively, transgenic animals may be constructed or commercially obtained, where the animals have germline alterations in one or more ion channel genes. Cells and tissues derived from such transgenic animals are used a source of cells for primary cultures.

Examples of transgenic animals having altered ion channel genes are known in the art. See, for example, Babij et al. (1998) *Circ Res.* 83(6):668–78 overexpress the long-QT syndrome mutation gene in transgenic mice; Barry et al. (1998) *Circ Res.* 83(5):560–7 functionally knockout the transient outward currrent in mice expressing a dominant-negative Kv4 alpha subunit; Baumer et al. (1998) *Biochem Biophys Res Commun.* 249(3):786–90 overexpress the $Na^+$—$Ca^{++}$ exchanger; Agre (1998) *Proc Natl Acad Sci USA*. 95(16):9061–3 utilizes aquaporin null phenotypes; etc. Methods of creating transgenic animals, either knock-outs or knock-ins, are well known in the art and need not be discussed in further detail herein.

For introduction of exogenous ion channel genes, or for transcriptional activation of endogenous ion channel genes, nucleic acid sequences are used to produce functional ion channel polypeptides. For expression, an expression cassette is employed. The expression vector will provide a transcriptional and translational initiation region, which may be inducible or constitutive, where the coding region is operably linked under the transcriptional control of the transcriptional initiation region, and a transcriptional and translational termination region. These control regions may be native, or derived from exogenous sources. The availability of multiple ion channel subunit sequences allows in vitro reconstruction of functional channels, which may comprise different alpha and beta subunits. The individual components may be modified by sequence deletion, substitution, etc. to determine the functional role of specific domains.

Both stable and transiently expressing cell lines may be used. For transient expression, full length ion channel cDNAs may be combined with the appropriate vectors to form expression constructs of an individual channel; or synthetic mRNA may be made through in vitro transcription of the channel construct. mRNA is then injected, singly or in combination with interacting channel subunit mRNAs, into prepared cells, e.g. oocytes, and the cells allowed to express the channel for several days.

In many cases the functional ion channel will be heteromultimers. For example, heteromultimers are known to form between different voltage gated, outward rectifying potassium channel a subunits, generally comprising four subunits, and frequently associated with auxiliary, β subunits. Heteromultimers may have decreased or increased conductance relative to a homomultimer, and may be altered in response to beta subunits or other modulatory molecules.

Ion channels: A large number of ion channels are available for genetic manipulation, from many different species. Examples include channels from human and other mammals, from *D. melanogaster*, invertebrate species, amphibian species, etc. as known in the art. The sequences of such channels are publicly available, e.g. through Genbank, SwissProt, and other databases. Channels may be roughly classified according to the ion that is transported, usually $K^+$, $Cl^-$, $Na^+$ and $Ca^{++}$. Channels may be further categorized according to whether they are ligand gated or voltage gated, and by the number of transmembrane domains, pores, etc. A brief overview of some channel types is presented in Table 1, however, the list is in no way limiting, as there are thousands of sequenced channel genes available for genetic manipulation. Examples include:

| Extracellular Ligand Gated Channels | |
| --- | --- |
| 5-hydroxytryptamine-gated integral receptor channels | |
| extracellular ATP-gated receptor channels | |
| kainate-selective (non-NMDA) selective glutamate receptor- channels | |
| nicotinic acetylcholine-gated integral receptor channels | |
| inhibitory receptor channels gated by extracellular gamma-aminobutyric acid | |
| inhibitory receptor-channels gated by extracellular glycine | |
| Intracellular Ligand Gated Channels | |
| $Ca^{++}$ channels gated by arachidonate metabolites; by inositol 1,3,4,5-tetrabiphosphate | |
| caffeine sensitive $Ca^{++}$ release channels | ryanodine receptors |
| $Ca^{++}$-store repletion channels | |
| inositol 1,4,5-triphosphate-sensitive $Ca^{++}$ release channels | $InsP_3R$ |
| Calcium activated non-selective cation channels | |
| cation channels activated in situ by intracellular cGMP | |
| ATP binding and phosphorylation dependent $Cl^-$ channels | CFTR |
| volume regulated $Cl^-$ channels | p-glycoprotein $Cl_{Ca}$ |
| calcium activated chloride channels | |
| potassium channels activated by free fatty acids | |
| intracellular calcium activated potassium channels | $K_{Ca}$ |
| intracellular sodium-activated potassium channels | $K_{Na}$ |
| Inward Rectifier Channels | |
| intracellular ATP inhibited $K^+$ channels | |
| muscarinic-activated $K^+$ channels | |
| inward rectifier $K^+$ channels | $K_{IR}$ family |
| hyperpolarization-activated cation channels underlying inward currents $i_f$, $i_h$, $i_q$ | |
| mechanosensitive ion channels | |
| aquaporin channel family | |
| Voltage Gated Channels | |
| voltage gated $Ca^{++}$ channels | |
| voltage gated chloride channels | |
| A-type (transient outward) potassium channels | |
| delayed rectifier potassium channels | |
| beta subunits associated with voltage gated $K^+$ channels | |
| K+ channels related to *D. melanogaster eag* | |
| K+ channels related to *D. melanogaster shaker* subfamily | |
| K+ channels related to *D. melanogaster Shab* subfamily | |
| K+ channels related to *D. melanogaster Shaw* subfamily | |
| K+ channels related to *D. melanogaster Shal* subfamily | |
| muscarinic inhibited K+ channels underlying $I_M$ | |
| Voltage gated Na+ channels | |
| G protein linked receptors regulating ion channel activities | |

A large body of literature exists in the general area of ion channels. A review of the literature may be found in the series of books, "The Ion Channel Factsbook", volumes 1–4, by Edward C. Conley and William J. Brammar, Academic Press. An overview is provided of: extracellular ligand-gated ion channels (ISBN: 0121844501), intracellular ligand-gated channels (ISBN: 012184451X), inward rectifier and intercellular channels (ISBN: 0121844528), and voltage gated channels (ISBN: 0121844536). Hille, B. (1992) "Ionic Channels of Excitable Membranes", 2$^{nd}$ Ed. Sunderland MA:Sinauer Associates, also reviews potassium channels.

Biosensor: as used herein, refers to a cellular system capable of responding to an external stimulus, usually a chemical stimulus, by altering the membrane electrical potential or current flow; and further comprises an means of monitoring such a change in potential or current, e.g. a microelectrode, or other transducer. Biosensors may record a transmembrane potential, or the extracellular potential. In a preferred embodiment of the invention, an extracellular potential is taken as the output signal.

Electrical activity of cultured cells generally utilizes micropipette or microwire electrodes. The cells to be monitored are located on a suitable substrate, and a recording electrode (micropipette or microwire) is positioned to be in contact with the cell membrane. To directly measure the transmembrane potential, an intracellular recording, relative to a distant reference electrode, of the action potential is made by inserting a micropipette electrode through the membrane, which forms a tight seal to the electrode (see Breckenridge et al. (1995) *J. Neuroscience Res.* 42:266–276). Alternatively, a micropipette or microwire positioned in close proximity to the cellular membrane is used to record the extracellular AP.

The use of planar microelectrode arrays for cultured cell biosensors is of particular interest. Such arrays generally consist of a substrate of glass, plastic or silicon over which a conductor, e.g. gold, platinum, indium-tin-oxide, iridium, etc., is deposited and patterned. An insulating layer, e.g. photoresist, polyimide, silicon dioxide, silicon nitride, etc., is deposited over the conducting electrodes and interconnects and then removed in regions over the electrodes to define the recording sites. Cells are cultured directly on this surface and contact the exposed conductor at the deinsulated recording sites. Depending on the size of the electrodes and the cells, recordings of electrical activity can be from a single cell or populations of cells. Each electrode site is generally connected to the input of a high input impedance, low noise amplifier, with or without AC coupling capacitors, to allow amplification of the relatively small extracellular signals. Examples of such biosensors are described by Novak et al. (1986) *IEEE Transactions on Biomedical Engineering* BME-33(2):196–202; Drodge et al. (1986) *J. Neuroscience Methods* 6(6):1583–1592; Eggers et al. (1990) *Vac. Sci. Technol.* B8(6):1392–1398; Martinoia et al. (1993) *J. Neuroscience Methods* 48:115–121; Maeda et al. (1995) *J. Neuroscience* 15(10):6834–6845; and Mohr et al. (1996) *Sensors and Actuators B-Chemical* 34(1–3):265–269.

On example of a suitable biosensor is described in U.S. Pat. No. 5,810,725, to Sugihara et al., which utilizes a planar electrode that enables multi-point simultaneous stimulation and recording of nerve cells over a long time. The planar electrode has a multiplicity of electrodes for measurement of electric activities of nerve cells in an organism, and comprises an insulating substrate, a multiplicity of electrodes disposed thereon, a wiring section in which lead wires are installed from the electrodes, and an insulating layer covering the lead wires.

Figure 3:
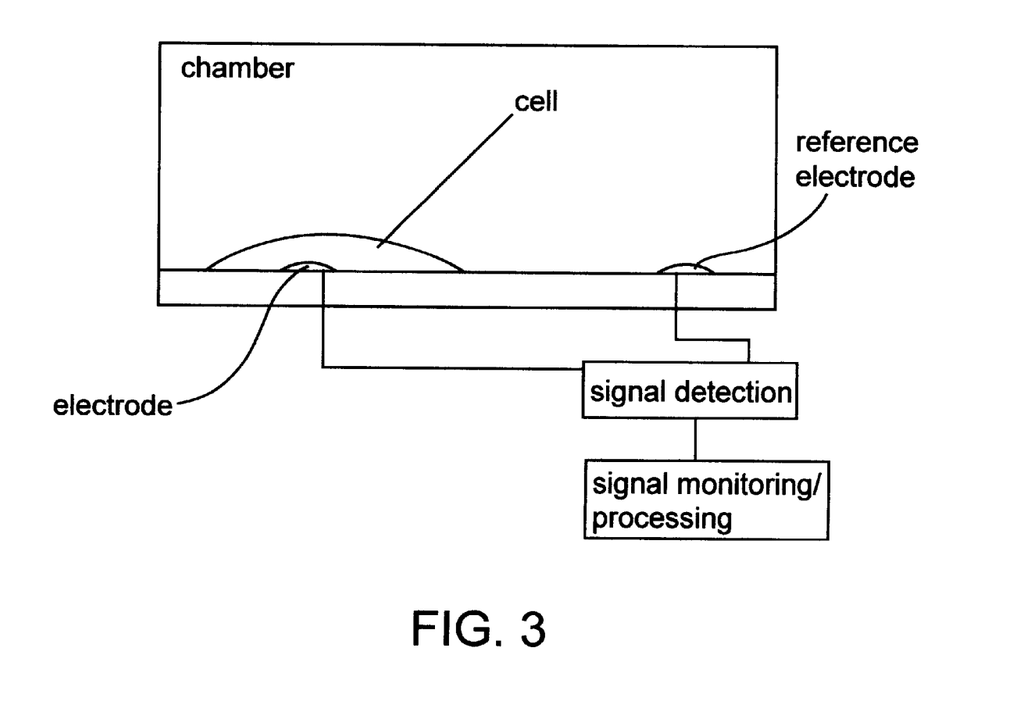
FIG. 3 is a block diagram of a system including processing means for spectral analysis.

In one embodiment of the invention, the biosensor comprises a system that includes a chamber used to culture cells, as shown in FIG. 3. For example, a standard Petri dish or equivalent structure is bonded to the monolithic structure to define a cell culture chamber. The monolithic structure includes an array of planar microelectrodes disposed on a substrate. The cell acts as a primary signal transducer, where the microelectrode acts as a secondary transducer of the signal. The detected signal is processed with monitoring and processing means in order to measure the voltage difference between each microelectrode and the reference electrode.

Each of the electrodes is sufficiently small to enable monitoring of an individual cell and its cellular membrane. In some embodiments, the diameter of the cell is larger than the diameter of the microelectrode. The specific size of the electrodes will vary according to the specific application, and the size of the cells being monitored. The surface of a single microelectrode of the array is exposed through a via in a passivation layer provided over a substrate.

The signal monitoring and processing means may be configured to perform a spectral analysis so as to monitor, in real time, cell action potential parameters. A signal monitoring and processing means, such as a personal computer, receives the detected signal through an analog/digital converter at a sample rate sufficient to read the detected sinusoidal signal. The system may perform spectral analysis of the resulting signals in order to monitor changes in various characteristics in real time.

The monolithic structures which include the microelectrode array may be packaged in various configurations. According to one example, arrays are fabricated on structures which are divided into individual 9×9 mm chips. The chips are packaged in a standard 40-pin ceramic dual in-line package, or any other types of package which contains a suitable number of leads. In this example, the bondwires are encapsulated (for mechanical and electrical robustness) in a nontoxic low stress epoxy. Bondwire encapsulation may also be achieved with polyurethane, polyethylene, wax, silicon carbide, silicon nitride, teflon, or polyimide.

Of course this construction may be modified in many different ways. For example, instead of dicing the arrays into multiple chips, the arrays can remain on the same substrate to form multiwell plates, each containing an array of electrodes. In such a configuration, Petri dishes are bonded to the substrate to define respective wells. The Petri dishes can comprise polystyrene, glass, polyethylene, teflon, metal, or any other type of polymer. The Petri dishes may be bound to a chip formed in accordance with the invention using conventional materials and techniques, such as epoxy, polyurethane, wax, or thermoplastic, using thermal or ultrasonic processes. In this alternate construction, bondwire connections can be eliminated by use of a substrate configured to mate directly with a connector, such as an edge card connector or pads for a standard pin type connector. Of course, this would require the substrate area to be significantly larger than the active electrode area.

Methods for Analysis of Compounds

The subject methods provide modulation reference patterns and databases of modulation reference patterns for a wide range of biologically active compounds. The reference patterns are then used for the identification and classification of test compounds. Evaluation of test compounds may be used to achieve different results.

In one aspect of the invention, the evaluation and comparison of modulation test patterns is used to identify an unknown compound. Such methods find particular use in conjunction with clinical and environmental testing. Environmental samples may comprise potential toxins or other biological hazards, where it is desirable to identify as quickly as possible the contaminants. Clinical samples may also comprise toxins, as well as pharmaceutically active drugs, microbial pathogens and by-products derived therefrom, and the like.

Where the sample to be tested may be a complex mixture of biologically active compounds, e.g. in blood samples, the identification process may utilize a subtraction step. The test sample is applied to a responsive cell using the previously described methods. However, in addition to obtaining the comparison of the spectral density signature against a negative control, the values may also be compared, or divided against, a "normal" sample, e.g. normal plasma, urine, etc. in order to isolate the effect of the potential test compound.

Alternative embodiments of the invention find use, in the classification of biologically active compounds, e.g. in the pharmaceutical industry for the evaluation of drug candidates. For these purposes it is of interest to determine the effect of a test compound against responsive cells having different complements of ion channels; and/or the range of effects in a family of compounds. For example, a series of analogs may be made to a known channel modulating agent, and the effect of this series of analogs determined by the subject methods.

The methods of the invention are also used for classification of unknown compounds as to their effect on a particular type of channel. In such cases the actual identification of a compound is not the desired goal, but merely to determine what the effect of the compound is on defined ion channels.

Databases of modulation reference patterns are developed using the above-described techniques, where such databases find use as a resource for the classification and identification of compounds.

It is to be understood that this invention is not limited to the particular methodology, protocols, cell lines, animal species or genera, constructs, and reagents described, as such may, of course, vary. It is also to be understood that the terminology used herein is for the purpose of describing particular embodiments only, and is not intended to limit the scope of the present invention which will be limited only by the appended claims.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

Materials and Methods

Figure 1:
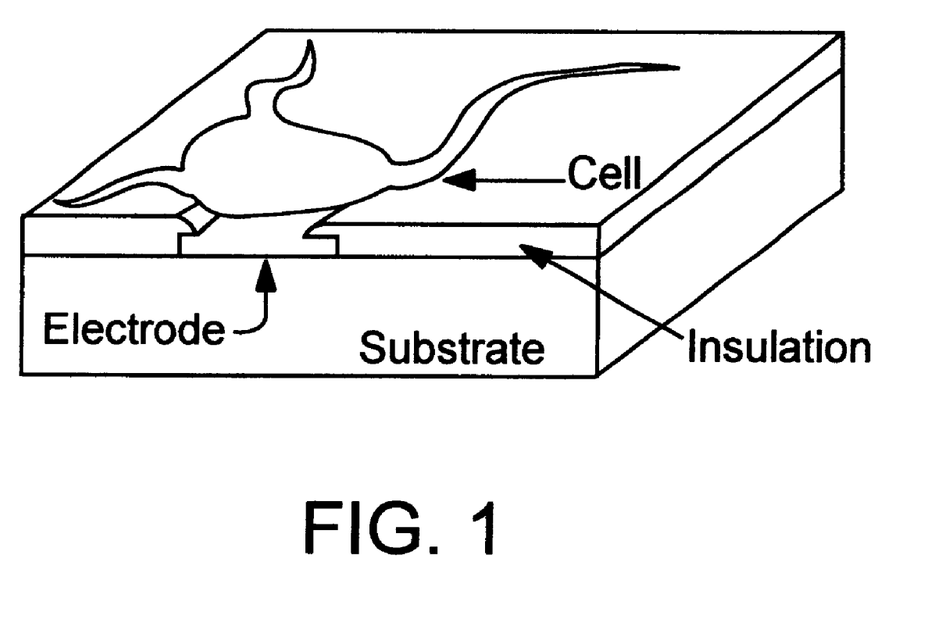
FIG. 1 illustrates an exemplary microelectrode and cell set-up.
Figure 2:
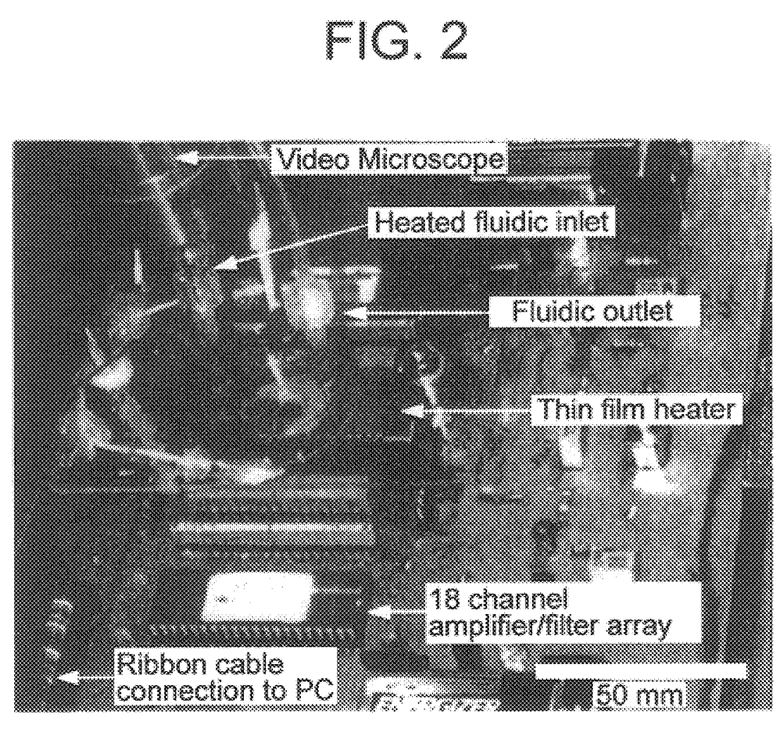
FIG. 2 illustrates a measurement setup used for action potential monitoring. The cell culture chamber is connected to the electronics via a ZIF socket. The amplified action potentials, through the 18 channel amplifier/filter arrays, are measured by direct connection to a PC via ribbon cables.

Microelectrode array. The microelectrodes used in these experiments consist of a 6×6 array of circular iridium, gold or platinum electrodes of varying areas (15 to 480 $\mu m^2$). The electrodes are fabricated on either glass or silicon substrates and have the basic structure shown in FIG. 1. The dice are packaged in a ceramic 40 pin dual in-line package (DIP), and bond-wire connections are made between the die and package. The bond-wires are encapsulated in a biocompatible epoxy that is also used to attach a polystyrene petri dish to form a cell culture chamber as shown in FIG. 2. Electrode impedances are reduced by electroplating platinum black on the electrode surface and using ultrasonic agitation to ensure adequate adhesion (Marrese (1987) *Analytical Chemistry* 59:217–218). The fabrication, packaging and platinizing procedures are described in detail in Borkholder et al. (1997) *Journal of Neuroscience Methods* 77:61–66. The packaged microelectrode arrays are used as a substrate for the culture of embryonic chick myocardial cells. These cells form a spontaneously beating syncytium which generates APs that travel through the cell layer. The electrical signals are monitored using the extracellular microelectrodes and low noise amplifiers.

Measurement System. Measurement of electrical activity from cultured cells in vitro requires a low noise amplification system coupled to data acquisition and storage equipment. The packaged microelectrode array is placed into the measurement system using a zero insertion force (ZIF) socket. Individual electrodes are AC coupled to a custom 18 channel amplifier/filter array (developed at Stanford University; Borkholder et al. (1996) *Conference Proceedings of the 1996 IEEE Engineering in Medicine and Biology*, Amsterdam, The Netherlands, 10/31–11/3, IEEE). The amplifier has a midband gain of 45 dB, input referred noise of 8 $\mu$V rms (10 Hz to 10 kHz), and an adjustable high pass filter (3 Hz to 10 kHz). The amplified AP signals are routed via ribbon cable to a PC-based data acquisition system capable of simultaneously monitoring up to 32 channels and storing the digital, 12-bit data to disk (Experimenter's Workbench 32 by DataWave Technologies, Colorado). Off-line analysis of the AP waveforms was performed using additional software tools.

In addition to the AP electronics, the measurement system must also include fluidics for sample introduction and temperature regulation. An indium-tin oxide (ITO) coated glass plate is positioned over the cell culture chamber. Electrical current flowing through the resistive ITO heats the glass to assist in temperature control and reduce condensation (to allow for visual observation of the cells). Holes drilled through the plate allow for insertion of a teflon coated thermistor probe, fluidic inlet and outlet tubes, and a platinum wire to be used as a grounded electrode in the solution. Fluid is heated to 37° C. prior to entering the dish using a resistive heater surrounding the inlet tube. The fluidic outlet consists of a 30 gauge needle connected to a vacuum source adjusted to match the inlet flow rate (2.0 ml/min). Die and package temperature is controlled by a thin-film heater positioned below the DIP. The combination of the heated glass plate, inlet fluid heating, and package heating result in a temperature at the electrode array of 37° C.±0.3° C.

Media flow, controlled by both gravity and tubing resistance, was adjusted to 2.0 ml/min. Manual sample selection was accomplished via a teflon 8-way valve configured to allow up to four different solutions to be used in the same experiment. HEPES buffered recording media was prepared for experiments at atmospheric $CO_2$ levels, with both the pH and osmolality adjusted to physiologic levels (7.3 and 300 mOsm/kg respectively). Where pharmaceuticals or toxins were to be tested, they were added directly to this recording media in concentrations which did not significantly alter the osmolality or pH of the solutions. Continuous flow was used to limit variations due to changing flow velocities and temperature which can be problematic with manual bolus injection systems.

Figure 4:
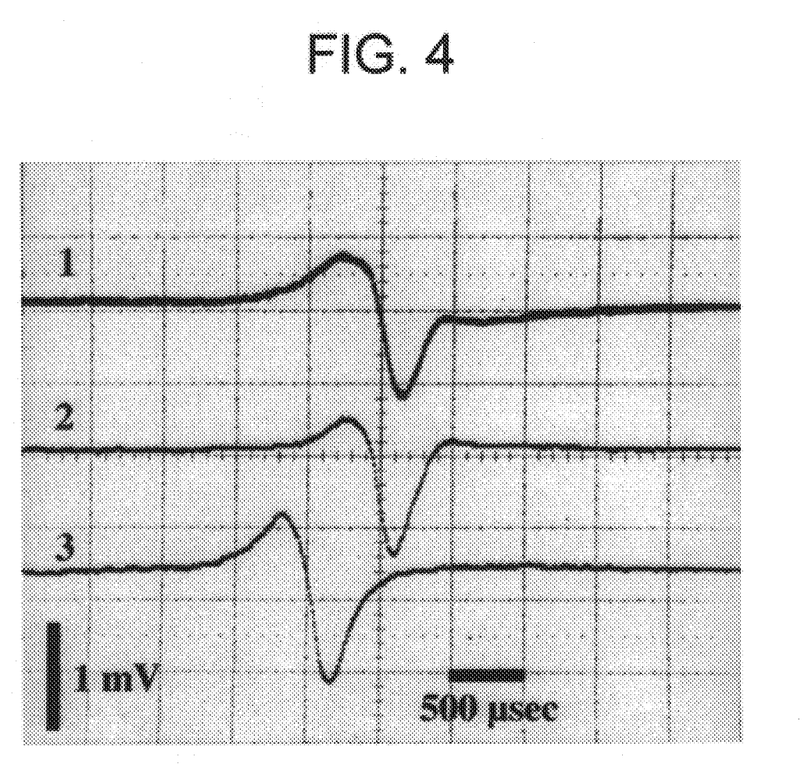
FIG. 4 shows the recording of spontaneous action potentials recorded extracellularly from the microelectrodes. The time delay observed between action potentials is due to the finite propagation velocity of the traveling action potential through the two dimensional sheet of cells.

Action Potential Measurement And Simulation. Embryonic chick myocardial cells were explanted from 11 day old chicks and plated onto the microelectrode arrays described above at a density of 1,000 cells/mm² using the techniques of De Hann; Barry; and Polinger (e.g. see Barry et al. (1975) *Circulation Research* 36:727–734). APs were measured from the spontaneously beating, two-dimensional sheet of cells two to four days after plating. Typical action potential recordings are shown in FIG. 4. Note the time delay between AP peaks, corresponding to the finite propagation velocity of the action potential wavefront through the tissue.

Correlation of these extracellular signals to classical intracellular recordings is often difficult since they represent a temporal derivative of the intracellular signal dependent on the coupling of the cell to the microelectrode. For tightly coupled cells, the extracellular signal looks like the first derivative of the intracellular. As the coupling is reduced, higher order derivatives are observed (Grattarola and Martinoia (1993) *IEEE Transactions on Biomedical Engineering* 40(1):3541). For the data presented herein, second order derivative characteristics have been confirmed by comparison to the time derivative of intracellular action potentials from cultured embryonic chick myocardial cells taken from the literature (Connolly et al. (1990) *Biosensors and Bioelectronics* 5:223–234).

Pharmaceutical Modulation. Action potentials are the result of a complex coordination of ionic flows through the cellular membrane. The flow of specific ions is controlled by voltage or ligand gating of ion channels which exhibit specificity in ion transport. The biological effect of many toxins and pharmaceuticals is often coupled to specific binding of the agent to receptors on the cell membrane. This can result in enhanced or inhibited opening of channels or direct blockage of the ion transport region. Thus, the relative impact of the different ions on the action potential can be modulated, resulting in changes in AP shape.

Three different pharmaceuticals and toxins were examined in this study: tetrodotoxin, epinephrine, and verapamil. Tetrodotoxin (TTX) is a naturally occurring neurotoxin that binds specifically to voltage gated $Na^+$ channels. It does not affect $Ca^{++}$ or $K^+$ channels, nor the $Na^+$ leakage that generally occurs through the non-gated channels and ion pumps of the resting cell membrane. The action of TTX may be easily modeled by adjustment of a scaling factor on the fast sodium current ($I_{Na}$).

Epinephrine is a natural hormone released by the adrenal gland which acts on both α- and β-adrenergic receptors. In cardiac tissue, this agonist acts mainly on β-adrenergic receptors causing modulation of several ionic currents through second messenger pathways (cyclic adenosine 3',5'-monophosphate (cAMP) mediated). Both the inward, long-lasting (L-type) $Ca^{++}$ current ($I_{Ca,L}$) and the outward, delayed rectifier-type $K^+$ current ($I_K$) are enhanced.

Figure 5:
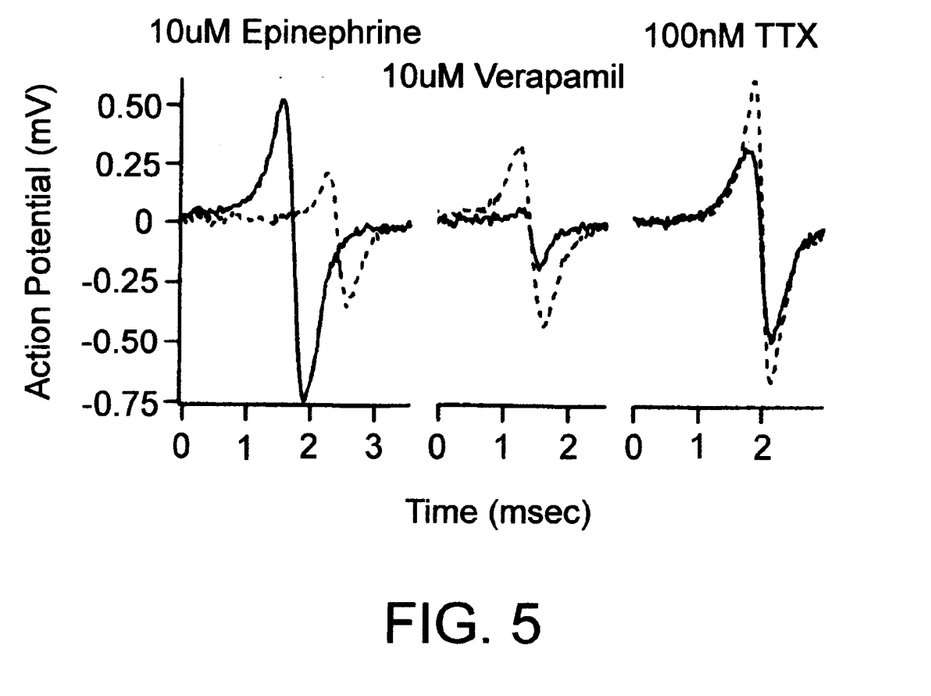
FIG. 5 shows a recording of action potential changes in the presence of pharmaceutical agents. Unmodulated APs are shown with dashed lines while post-agent action potentials are represented by solid lines. Epinephrine ($Ca^{++}$ channel agonist), verapamil ($Ca^{++}$ channel blocker), and tetrodotoxin (TTX) (fast-$Na^+$ channel blocker) effects are shown. The waveforms presented are extracellular recordings from a spontaneously beating culture of embryonic chick myocardial cells cultured on a planar microelectrode array. They represent the second temporal derivative of the intracellular signal.

Verapamil is a lipid-soluble compound that preferentially blocks L-type $Ca^{++}$ channels. It not only reduces the magnitude of the $Ca^{++}$ current, but also decreases the rate of recovery of the channel. When applied at high enough doses (tens of $\mu$M), verapamil can also affect voltage-gated $K^+$ channels resulting in enhanced inactivation of the rectifying $I_K$ current (Pancrazio et al. (1991) *Journal Of Pharmacology and Experimental Therapeutics* 257:184–191. From the actual data shown in FIG. 5, it is clear that the compounds tested had a significant and distinct impact on the action potential shape. It is important to note that both epinephrine and verapamil tend to affect the plateau phase of the action potential, which is difficult to observe in the second derivative.

Power Spectral Density Analysis. To examine how the spectral characteristics of the action potentials change, the power spectral density (PSD) of each waveform was taken both before and after addition of the biologically active compound. This PSD was estimated by first taking the fast fourier transform (FFT) of the waveform, multiplying the FFT result by its complex conjugate and dividing by the frequency range. This was done for waveforms both before and after addition of the agent of interest. A modulation function for the pharmaceutical was then determined by dividing the PSD after agent addition by the PSD before agent addition. This ratio has been plotted for the experimental results in FIG. 6.

Figure 6:
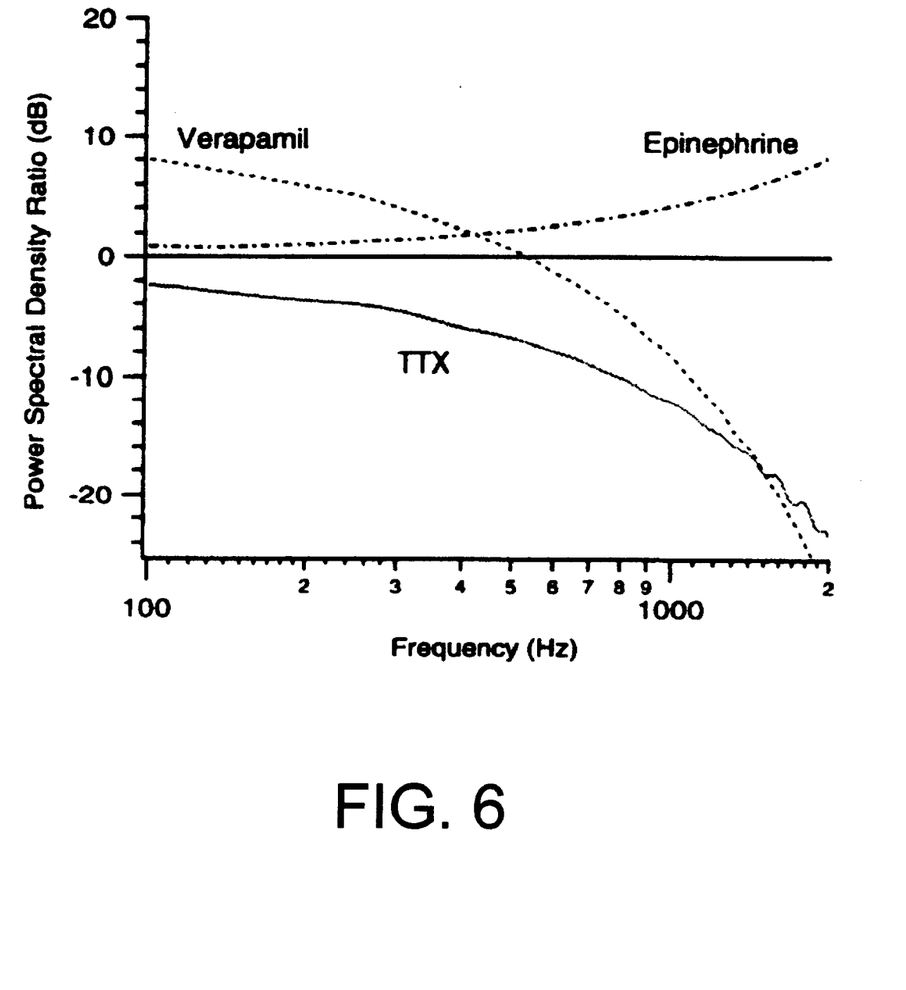
FIG. 6 shows power spectral density (PSD) ratio plots (PSD after agent÷PSD before agent). Additions of 10 $\mu$m epinephrine ($Ca^{++}$ channel agonist), 100 nM tetrodotoxin (TTX) ($Na^+$ channel blocker), and 10 $\mu$M verapamil ($Ca^{++}$ channel blocker) are all shown to have different effects on the PSD of the measured action potential. 8 channels of data were averaged with error bars of one sigma.

As can be seen from the experimental results of FIG. 6, there were characteristic modulation functions observed for each of the compounds tested. Epinephrine enhanced the power of the AP across a 2 kHz bandwidth with a slight bandpass effect observed. Verapamil had the opposite effect, reducing the overall AP power, again with a bandpass signature. Tetrodotoxin exhibited a low pass filter effect that clearly reduced the high frequency components of the AP. Additional data using a fast and slow $Na^+$ channel blocker (QX-314) resulted in a modulation function similar to that of TTX, but with additional attenuation at lower frequencies. These results show definite, unique characteristic responses for the agents tested. The similarity between the modulation functions for TTX and QX-314 is further evidence that unique curves exist for different classes of ionic channels.

The effects of three different biologically active agents (tetrodotoxin, verapamil and epinephrine) on the action potentials of spontaneously beating chick myocytes cultured on planar microelectrode arrays have been examined. The power spectral density of these APs revealed unique modulation functions associated with action on specific classes of ion channels. Simulated action potential and PSD results matched those for tetrodotoxin well as expected given the second derivative nature of the measured signals.

The experimental results described above demonstrate the utility of the present invention as a tool for pharmaceutical and toxin screening. Specifically, in place of TTX, any analyte may be assayed for the effect or impact that addition of the analyte to the cell culture medium will have upon the electrical characteristics of the cell. As noted elsewhere in the specification, the analyte can be one or more materials selected from the group consisting of pharmaceutical agent, drug, environmental factor, toxin, chemical agent, biological agent, and virus.

What is claimed is:

1. A method for characterizing the effect of a test compound on membrane electric potential or current in an excitable cell, the method comprising:

contacting a biosensor with said biologically active test compound; and separately contacting said biosensor with a reference compound, wherein said biosensor comprises at least one transducing means and one or more excitable cells in vitro in operable contact with said transducing means, which is connected to a signal detecting means;

recording the change in membrane electric potential or current in said excitable cells as a result of introduction of said test compound and said reference compound by said signal detecting means to provide an output signal;

deriving a modulation test pattern from the output signal resulting from said test compound and deriving a modulation reference pattern from the output signal resulting from said reference compound;

comparing said modulation test pattern to said modulation reference pattern to determine the presence of a statistically significant variation between said patterns in order to characterize the effect of said compound according to its effect on membrane electric potential or current in an excitable cell, wherein a statistically significant variation between said modulation test pattern and said modulation reference pattern indicates a difference between said test compound and said reference compound.

2. The method of claim 1, wherein said change in membrane electric potential in said excitable cells comprises one or more subthreshold events.

3. The method of claim 1 wherein said change in membrane electric potential in said excitable cells comprises one or more action potentials.

4. The method of claim 1, wherein said change in membrane electric potential is spontaneous.

5. The method of claim 1, wherein said change in membrane electric potential is stimulated with electric current or voltage.

6. The method of claim 1 wherein said test compound is present in an environmental sample.

7. The method of claim 1 wherein said test compound is present in a clinical sample.

8. The method of claim 1 wherein said test compound is a drug candidate.

9. A method for characterizing the effect of a test compound on membrane electric potential or current in an excitable cell, the method comprising:

contacting a biosensor with said biologically active test compound; and separately contacting said biosensor with a reference compound, wherein said biosensor comprises at least one transducing means and a first one or more excitable cells in vitro in operable contact with said transducing means, which is connected to a signal detecting means;

recording the change in membrane electric potential or current in said excitable cells as a result of introduction of said test compound and said reference compound by said signal detecting means to provide an output signal;

deriving a modulation test pattern from the output signal resulting from said test compound and deriving a modulation reference pattern from the output signal resulting from said reference compound wherein said modulation reference pattern and said modulation test pattern each comprise one or more power spectral density values;

comparing said modulation test pattern to said modulation reference pattern to determine the presence of a statistically significant variation between said patterns in order to characterize the effect of said compound according to its effect on membrane electric potential or current in an excitable cell, wherein a statistically significant variation between said modulation test pattern and said modulation reference pattern indicates a difference between said test compound and said reference compound.

10. The method of claim 9, wherein said modulation reference pattern and said modulation test pattern each comprise one or more comparisons of power spectral density values against a control power spectral density value.

11. The method of claim 10, wherein said control comprises the power spectral density obtained for said excitable cells in the absence of an introduced biologically active compound.

12. The method of claim 10 wherein said control comprises the power spectral density obtained for an excitable cell that is different from said first excitable cell in its complement of ion channels, in the presence of said biologically active agent.

13. The method of claim 9, wherein said excitable cells comprise primary cultured cells.

14. The method of claim 9, wherein said cells are obtained from a transgenic animal comprising a germline alteration in one or more ion channel genes expressed in said excitable cells.

15. The method of claim 9, wherein said excitable cells comprise a cell line.

16. The method of claim 15, wherein said cell line is genetically modified to introduce or delete one or more ion channel genes normally expressed in said cell line.

* * * * *